United States Patent [19]

Coassin

[11] Patent Number: 5,405,585
[45] Date of Patent: Apr. 11, 1995

[54] FLUID DELIVERY SYSTEM UTILIZING MULTIPLE PORT VALVE

[75] Inventor: Peter J. Coassin, San Juan Capistrano, Calif.

[73] Assignee: Beckman Instruments, Inc., Fullerton, Calif.

[21] Appl. No.: 277,299

[22] Filed: Apr. 12, 1994

Related U.S. Application Data

[63] Continuation of Ser. No. 909,232, Jul. 6, 1992, abandoned.

[51] Int. Cl.⁶ .................................................. B01L 3/02
[52] U.S. Cl. .................................... 422/100; 422/81; 422/99; 422/112; 422/116; 435/6; 435/289; 436/89; 137/625.19
[58] Field of Search .................. 137/625.19; 422/80, 422/81, 99, 100, 102, 112, 116; 435/6, 255, 289; 436/89

[56] References Cited

U.S. PATENT DOCUMENTS

| | | | |
|---|---|---|---|
| 2,898,937 | 8/1959 | Williams | 137/625.19 |
| 3,008,491 | 11/1961 | Riefler | 137/625.19 |
| 3,536,451 | 10/1970 | Ludwin | 137/625.19 |
| 3,554,224 | 1/1971 | Kirk | 137/625.19 |
| 3,647,390 | 3/1972 | Kubodera et al. | 422/116 |
| 3,896,029 | 7/1975 | Beuselinck | 137/625.19 |
| 4,399,105 | 8/1983 | Tilgner et al. | 422/111 |
| 4,458,066 | 7/1984 | Caruther et al. | 536/27 |
| 4,500,707 | 2/1985 | Caruther et al. | 536/27 |
| 4,569,236 | 2/1986 | Kitchen et al. | 137/625.19 X |
| 4,598,049 | 7/1986 | Zelinka et al. | 435/287 |
| 4,602,657 | 7/1986 | Anderson et al. | 137/625.19 X |
| 4,746,490 | 5/1988 | Saneii | 422/62 |
| 4,826,763 | 5/1989 | Norris et al. | 435/68 |
| 4,863,849 | 9/1989 | Melamede | 435/6 |
| 5,038,852 | 8/1991 | Johnson et al. | 422/116 X |
| 5,053,454 | 10/1991 | Judd | 422/116 X |
| 5,108,928 | 4/1992 | Menard et al. | 436/43 |
| 5,112,575 | 5/1992 | Whitehouse et al. | 422/116 |
| 5,137,695 | 8/1992 | Rusnak et al. | 422/116 |
| 5,164,159 | 11/1992 | Hayashi et al. | 422/81 |

FOREIGN PATENT DOCUMENTS 2146030  4/1985  United Kingdom .

OTHER PUBLICATIONS

Patent Astracts of Japan—JP60089493 and 85-156914 20 May 1995.

*Primary Examiner*—James C. Housel
*Assistant Examiner*—Harold Y. Pyon
*Attorney, Agent, or Firm*—William H. May; P. R. Harder

[57] ABSTRACT

The present invention is directed to the implementation of a multi-port rotary valve in an automated chemistry processing instrument which reduces chemical reagent cross contamination and simplifies system design and control. One or more multi-port rotary valves are used in conjunction with isolation valves which are each dedicated for an associated reagent in the system. According to one embodiment of the present invention, the instrument utilizes a multi-port valve which defines several fluid branches each associated with a reagent. The valve has a common inlet and common outlet which are selectively brought into fluid communication with the branches in a controlled sequence. At each branch, there is a two-way three-port isolation valve which controls introduction of an associated reagent into the branch. When a branch is selected by the rotary valve, the reagent introduced into the branch is delivered out of the common outlet by the flow from the common inlet. According to another embodiment of the present invention, the reagents are introduced through isolation valves between two multi-port rotary valves.

10 Claims, 6 Drawing Sheets

FLUID DELIVERY SYSTEM UTILIZING MULTIPLE PORT VALVE

The present application is a continuation of U.S. application Ser. No. 07/909,232 filed Jul. 6, 1992, now abandoned.

BACKGROUND OF THE INVENTION

1. Field of the Invention

The present invention relates to fluid delivery systems, and more particularly to multiple port fluid delivery systems for use in automated chemistry processing instruments.

2. Description Of Related Art

For fluid delivery systems designed for handling several types of fluids in a flow system, one of the design concerns is to reduce cross contamination between the fluids. Especially for systems handling chemical reagents, cross contamination between different reagents often adversely affects the chemical integrity of the reagents and thus the efficiency of the controlled chemical reactions that involve such reagents. For example, in an automated nucleic acid synthesis instrument, various steps are carried out by a reagent delivery system which dispenses a number of chemical reagents in a predetermined sequence in a cycle into a synthesis reaction column, in accordance with instructions from the system controller or computer. The synthesis efficiency depends in part on the integrity of the reagents.

As a background, the chemistry of nucleic acid synthesis (generally referred to as "DNA synthesis") is well known. Generally, this is the process of constructing synthetic single-stranded oligonucleotide through linking of various nucleotides which are the basic building blocks of DNA. DNA synthesis is described generally in U.S. Pat. No. 4,458,066 issued to Caruthers et al, entitled "Process for Preparing Polynucleotides", which is incorporated by reference herein. The process described therein constructs a single-stranded oligonucleotide using one of several approaches in synthesizing DNA, namely the so-called solid-phase phosphoramidite method which generally involves the steps of deblocking/activation, coupling, capping and oxidation in each synthesis cycle for linking a building block on a solid-phase support. Further reference to this process of DNA synthesis may be found in "Oligonucleotide Synthesis - A Practical Approach" edited by M. J. Gait, IRL Press, 1984, which is incorporated by reference herein; and in particular Chapter 3 therein entitled "Solid-Phase Synthesis of Oligodeoxyribonucleotide by the Phosphite-Triester Method" written by Tom Atkinson and Michael Smith. It is suffice to understand for purpose herein that the reagents are delivered to the reaction column via several valves.

The effectiveness of the DNA synthesis process is very sensitive to the purity of the reagents. Cross contamination between the reagents adversely affects the production of oligonucleotide. One source of cross contamination is in the valves, particularly multi-port valves which select delivery between different reagents. There are inevitable dead volumes in the valves associated with switching between reagents. For this reason, past instrument designs which have required absolute control over cross-port contamination and random selection of chemical reagents have avoided use of multi-port valves because of the difficulties in preventing such contamination. However, the adopted design of the fluid delivery system is relatively complex and requires additional effort in designing the control scheme for the system.

SUMMARY OF THE INVENTION

The present invention is directed to the implementation of a multi-port rotary valve in an automated chemistry processing instrument which is configured to reduce chemical reagent cross contamination and simplifies system design and control. One or more multi-port rotary valves are used in conjunction with isolation valves which are each dedicated for an associated reagent in the system.

According to one embodiment of the present invention, the instrument utilizes a multi-port valve which defines several fluid branches each associated with a reagent. The valve has a common inlet and common outlet which are selectively brought into fluid communication with the branches in a controlled sequence. At each branch, there is a two-way three-port isolation valve which controls introduction of an associated reagent into the branch. When a branch is selected by the rotary valve, the reagent introduced into the branch is delivered out of the common outlet by the flow from the common inlet.

Several such combination of rotary plus isolation valves may be linked in tandem or in parallel to accommodate a larger number of different reagents.

According to another embodiment of the present invention, the reagents are introduced through isolation valves between two multi-port rotary valves.

DETAIL DESCRIPTION OF THE ILLUSTRATED EMBODIMENT

The following description is of the best contemplated mode of carrying out the invention. This description is made for the purpose of illustrating the general principles of the invention and should not be taken in a limiting sense. The scope of the invention is best determined by reference to the appended claims.

While the present invention is described in the context of DNA synthesis, it is to be understood that the present invention can be implemented for other chemical processes, e.g. peptide and protein synthesis, protein sequencing and oligosaccharide synthesis and sequencing, as well as any system requiring integrated delivery of different reagents.

Figure 1:
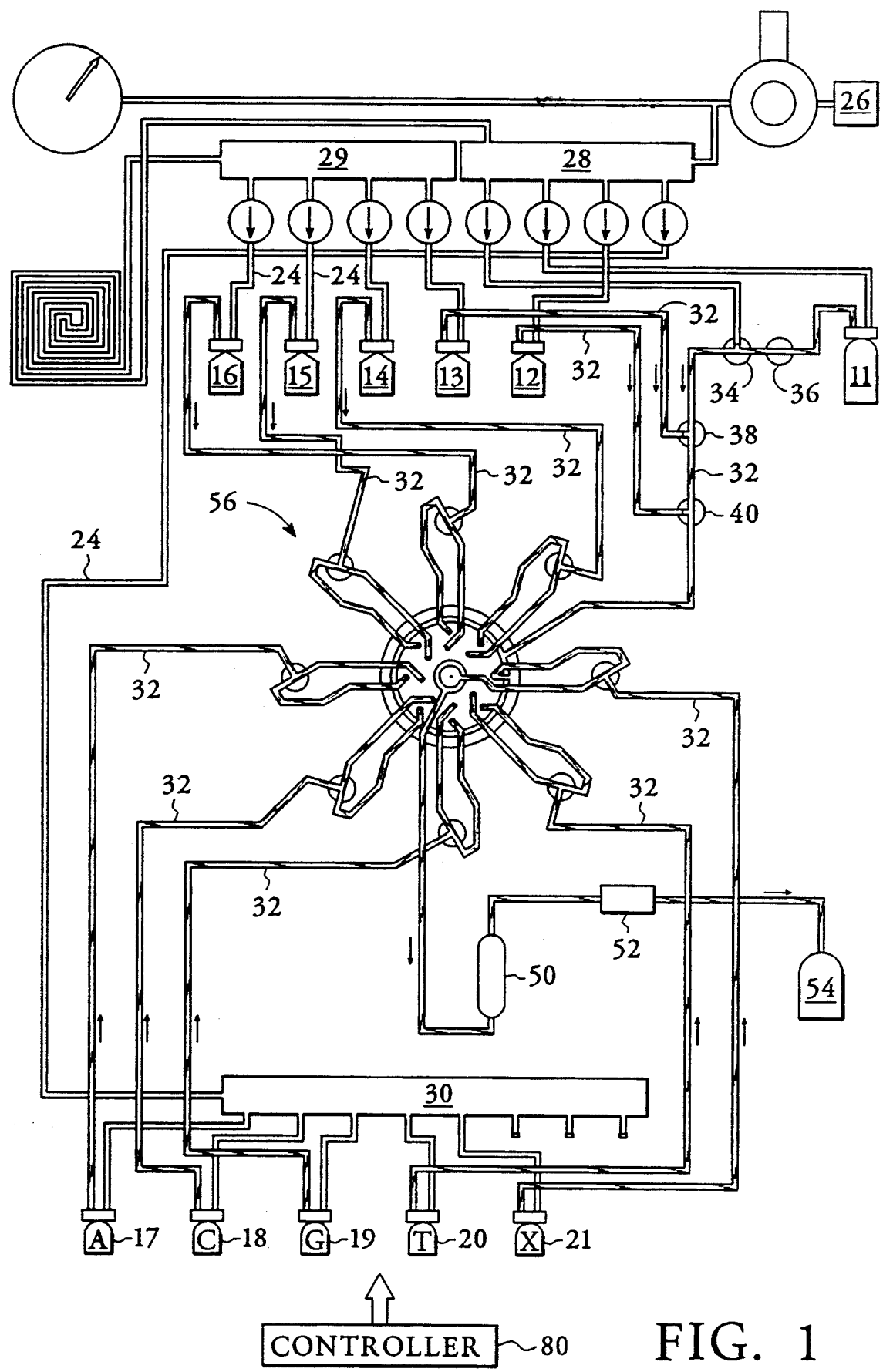
FIG. 1 is a simplified schematic fluid diagram of an automated nucleic acid synthesis instrument which incorporates the fluid delivery system in accordance with one embodiment of the present invention.
Figure 1A:
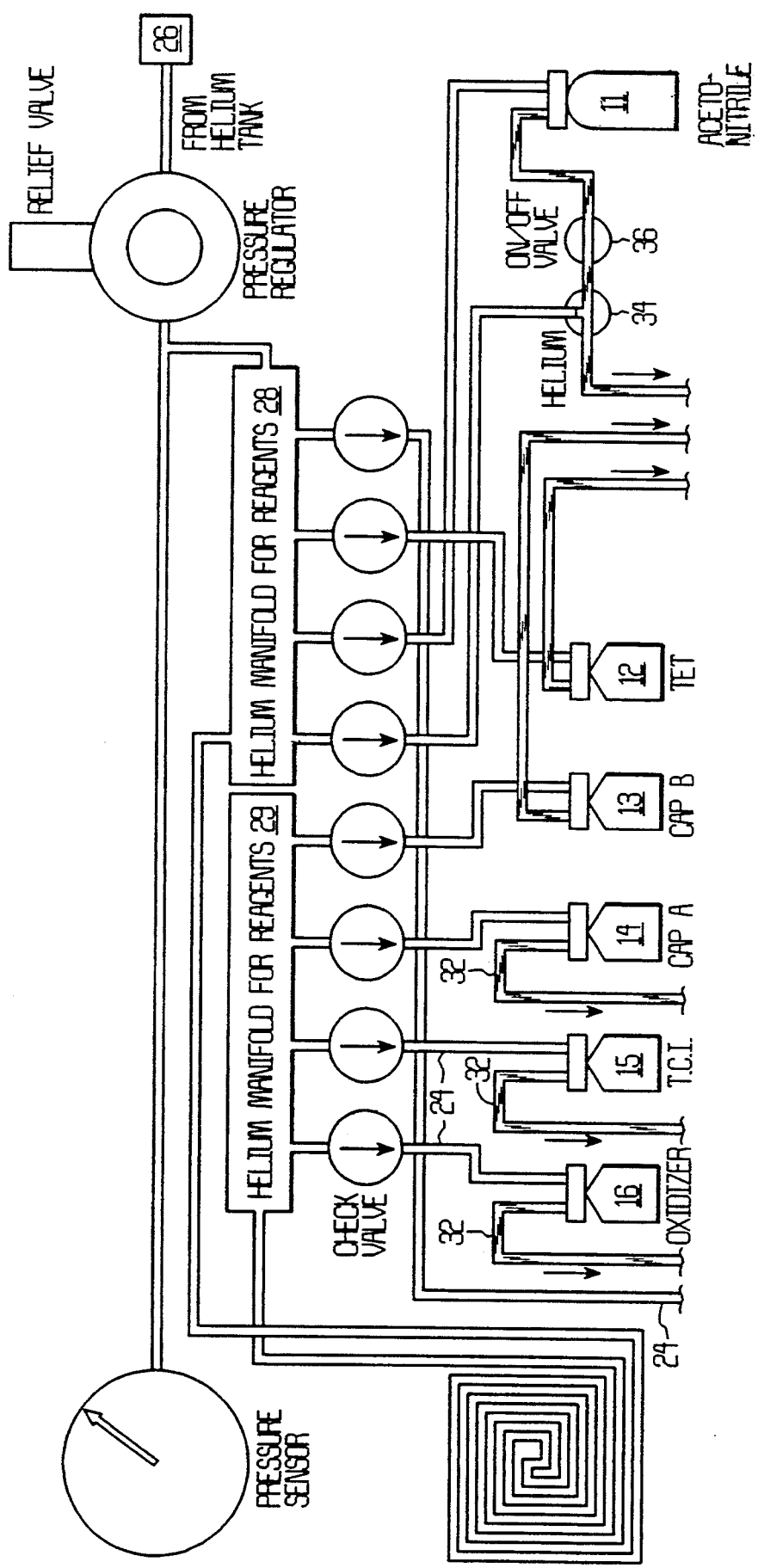
Figure 1B:
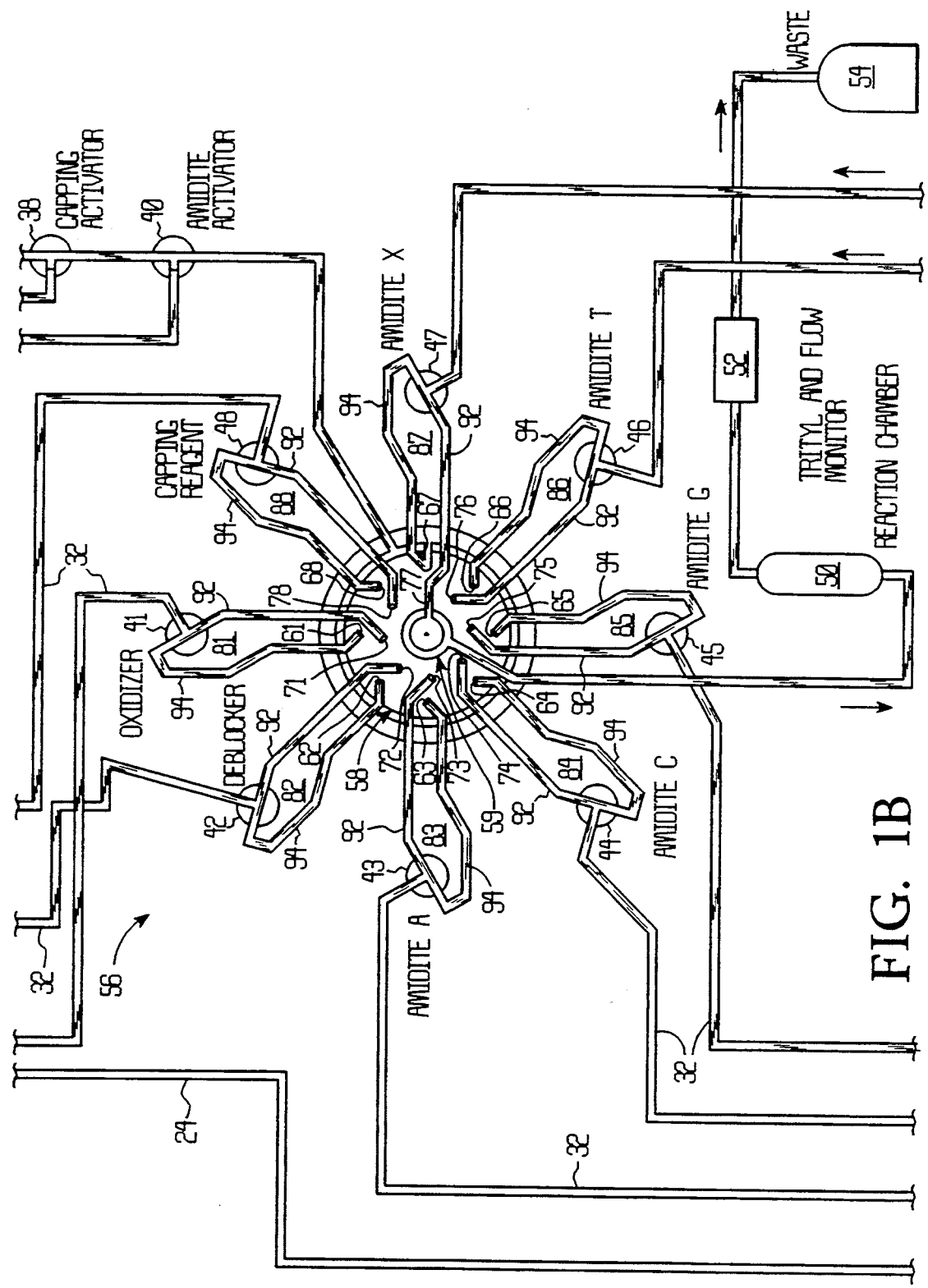
Figure 1C:
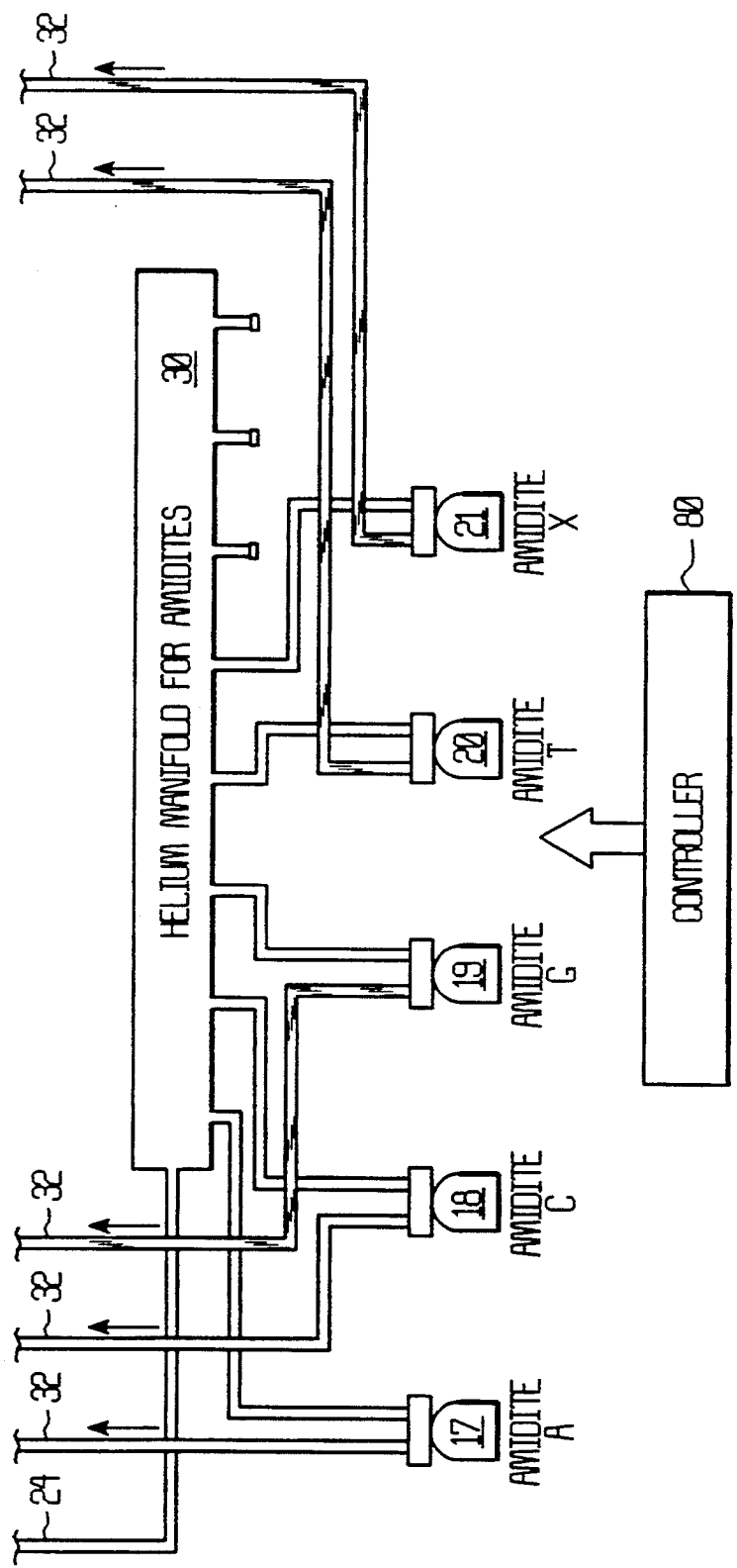
Figure 1D:
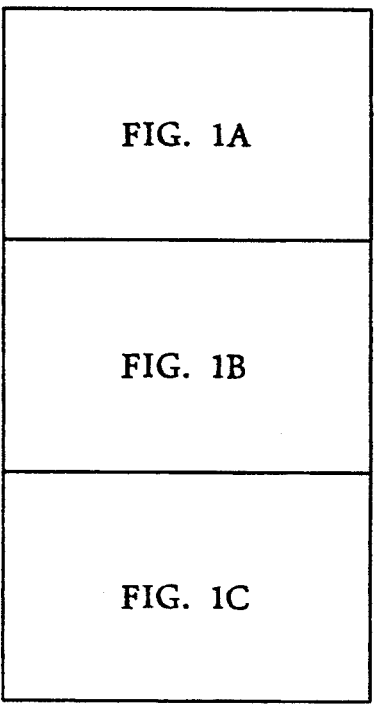

FIG. 1 illustrates the simplified schematic arrangement of an automated chemical processing apparatus suitable for use to synthesize DNA. This is a simplified fluid diagram for the purpose of illustrating the basic concept of the invention. A fully automated apparatus typically comprises more reagent reservoirs and additional flow components. It is within the knowledge of one skilled in the art to incorporate the necessary reagent reservoirs and flow components to build an automated DNA synthesizing apparatus which incorporates the present invention in light of the disclosure of U.S. Pat. No. 4,458,066 to Caruthers et al which has been incorporated by reference herein.

Referring to FIG. 1, reservoirs 11 to 21 contain appropriate chemical reagents for DNA synthesis, e.g. acetonitrile (solvent), tetrazole, oxidizer, capping activators, amidire activator, deblocker, and various amidites. Each reservoir is capped. Tubings 24 that are unshaded in FIG. 1 are gas lines which deliver a pressurized inert gas such as helium from a tank 26 to above the reagent level in each reservoir. Manifolds 28 to 30 are provided to distribute the pressurized gas to the reservoirs 11 to 21. Tubings that are shaded in FIG. 1 are for reagent transport. The tubings 32 have ends immersed in the reagents and are connected to valves 36, 38, 40, 41 to 48 which turn on and off fluid delivery from the reservoirs. As will be described in greater detail below, some of the tubings 32 are connected to isolation valves 41 to 48 which control the flow through the tubings. When an isolation valve is actuated, the reagent in the reservoir connected to that valve will be forced into the connected tubing and through the valve by the pressurized gas. The valve 36 is a normally-closed two port valve. When it is actuated, it permits flow through the valve. When it is released, it blocks flow through the valve. The valves 38 and 40 are two-way three-port valves similar to the isolation valves 41 to 48 described below.

An additional valve 34 is provided at a point in the fluid system which is connected to the pressurized gas tank 26. When this valve is actuated, gas is injected into the flow stream to interrupt the continuity of the chemical reagent flow.

Near the downstream end of the system is a chemical reaction chamber 50 which is designed to facilitate the desired chemical reactions to take place, in the example described herein, the synthesis of nucleotides. Further downstream is a detector positioned along or adjacent the flow path to monitor system performance from the passing fluid flow. At the very end of the flow system, a waste container 54 is provided to collect the spent reagents that have flowed through the system, or a collection device (not shown) is provided if so desired to collect any reaction end products from the chemical reactions.

Figure 2:
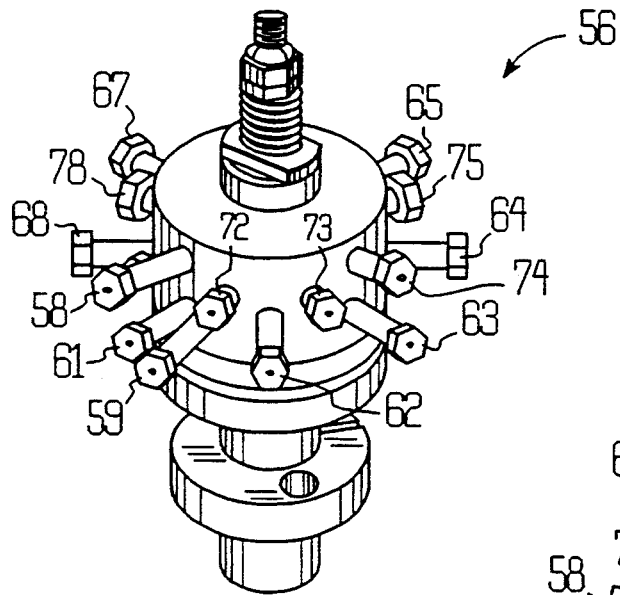
FIG. 2 is perspective view of the rotary valve used in the fluid delivery system.
Figure 3:
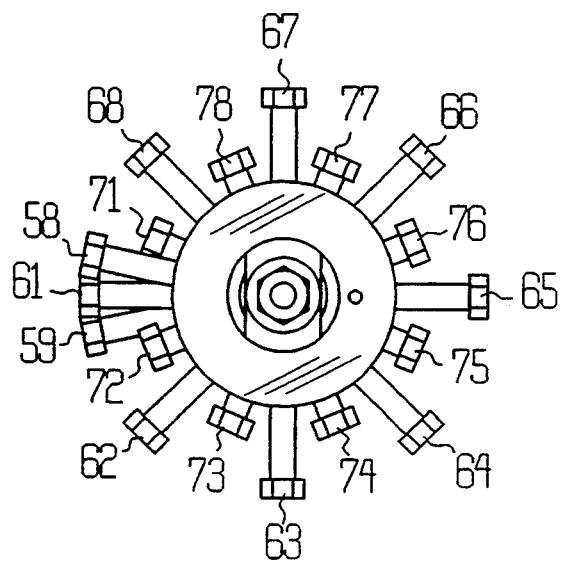
FIG. 3 is a top view of the rotary valve.

The control of the delivery of the various reagents to the reaction chamber is effected by a combination of a multi-port rotary valve 56 and several isolation valves 41 to 48. Referring also to FIGS. 2 and 3, the multi-port valve 56 has a common inlet 58 and a common outlet 59, and in the example shown eight pairs of branch inlet ports 61–68 and outlet ports 71–78 which are coupled to fluid branches 81–88 (see FIG. 1). Rotary valves with more ports may be used depending on the system requirements. The valve 56 has a rotary valve element which selectively brings the common inlet 58 and common outlet 59 into fluid communication with the pairs of branch inlet and outlet ports (61–68, 71–78) in a controlled sequence (FIG. 1 shows branch 87 being accessed). The multi-port rotary valve 56 is available from Valco Instruments Co. Inc. in Houston, Tex., U.S.A (part no. CST8P).

In each branch (81–88), there is a two-way three-port isolation valve (41–48) which controls introduction of an associated reagent into the branch. When one of the isolation valves is actuated, its three valve ports are opened, so that flow may occur in any direction through any port. When the valve is released, only the port connected to the associated reservoir is closed. The valves are of the electromechanical type which are actuated under control by controller 80. The valves are available from General Valve Corp. in Fairfield N.J, U.S.A. (part no. 2-104-900). The valves 41 to 48 are connected to the inlet and outlet ports (61–68, 71–78) by tubings 92 and 94 as shown in FIG. 1.

FIG. 1 shows the valve 56 accessing the branch 87. In this position, the flow path from the solvent (acetonitrile) reservoir 11 passes through valves 36, 34, 38 and 40, the common inlet 58 of valve 56, the branch inlet port 67, the tubing 94 in branch 87, the isolation valve 47, the tubing 92 in branch 87, the branch outlet port 77, the common outlet 59 of valve 56, the reaction chamber 50, to the waste container 54. As the rotary valve 56 accesses other branches, the flow path would be through those branches in a similar manner.

When a branch (81–88) is selected by the rotary valve 56, the reagent introduced into the branch is delivered out of the common outlet 59 along the flow from the common inlet 58. Specifically, in operation, a solvent 11 (in this example acetonitrile) is supplied through the main flow to the common inlet 58 of the rotary valve 56 and initially floods all the branch flow passages 92 and 94 by rotating the valve to each branch in sequence. Thereafter, a particular reagent in a reservoir is delivered to the reaction chamber 50 by the following sequence of steps: first, rotating the valve 56 to select access to the pair of inlet and outlet ports (6–68, 71–78) associated with the reagent; second, activate the associated isolation valve (41-48) to introduce the reagent into the fluid branch (81–88) which mixes with the solvent (the on-off valve for the solvent may be turned off to stop the main flow during reagent introduction); third, release the isolation valve to stop reagent flow; fourth, pump a quantity of solvent through the fluid branch to displace the bolus of reagent from the fluid branch to the reaction chamber 50 and at the same time flush the fluid branch and the valve element to remove traces of the reagent; fifth, rotate valve 56 to another port for another reagent. It is noted that the branch last accessed by the rotary valve 56 is filled with solvent at the end of delivering the reagent out of the fluid branch.

The rotary valve 56 and the valves 41 to 48 are actuated in appropriate synchronization to deliver the reagents needed to complete each synthesis cycle. The synchronization of valve actuations as well as other system functions are controlled by a programmable controller, the detail of which is not described herein as one can easily implement the control function given the desired operations to be accomplished.

The aforedescribed configuration eliminates cross contamination between different reagents. The dead volumes with this type of configuration are substantially less than implementations involving discreet valves linked together by means of common fluid ports to provide chemical reagent delivery to a common reaction site. It is estimated that such a configuration with 0.020" I.D. tubing can lead to system dead volumes of 50 μL or less. Moreover, in the present configuration, the default or fail safe position (i.e. the branches with isolation valve off in a state filled with solvent) provides a wash circuit, eliminating additional steps to implement a system wash function. It has been found that the present reagent delivery system configuration accounts for 35 to 50% savings in consumption of phosphoramidites than other DNA synthesizer. Phosphoramidites cost a customer on the order of $250 for 2 grams or approximately a two-week supply for a typical user.

It is preferred that the tubings 92 and 94 are smaller in flow diameter than that of the reagent input tubings 32. This reduces the flow volume in the fluid branch 81–88 so that it takes less solvent for flushing the tubings. It is also preferred that the length of the sections of the tubings 92 and 94 between the isolation valves 41–48 and the respective inlet and outlet ports 61–68 and 71–78 are substantially the same. This ensures that for those reagents introduced to the main flow via the rotary valve 56, the distance to reach the reaction chamber 50 is constant. Further, it is preferred that the length of the sections of tubings 32 leading from the reagent reservoirs 14–21 to the respective isolation valves 41 to 48 are substantially the same. In other words, the reagents are arranged in a circular symmetrical configuration with respect to a central delivery hub (the rotary valve 56). Differences in fluid path lengths and resistances are eliminated. Control of multiple reagent flow rates and the effects of pressure drop on relative flow rate from the different reagents are normalized by this symmetrical configuration. Any drift in fluid flow parameters would be consistent for the different reagent branches.

The basic configuration described above may be built upon to handle larger number of different reagents. For example, two or more of such configuration of rotary valve plus isolation valves may be connected in parallel, i.e. sharing one main flow input to the inlets of the rotary valves and one or more outputs for multiple reagent delivery site. Also, two or more of such configuration can be linked in tandem wherein the output of an upstream rotary valve is the input of a downstream rotary valve. Further, two or more of such configuration can be connected in a manner in which one or more of the isolation valves in a rotary valve is replaced with a rotary valve having associated isolation valves. Still further, the configuration may be used in "reverse" to create multiple delivery sites at the branches with one main reagent input to the rotary valve. Conceivably, any combination of the foregoing implementation may be possible.

Figure 4:
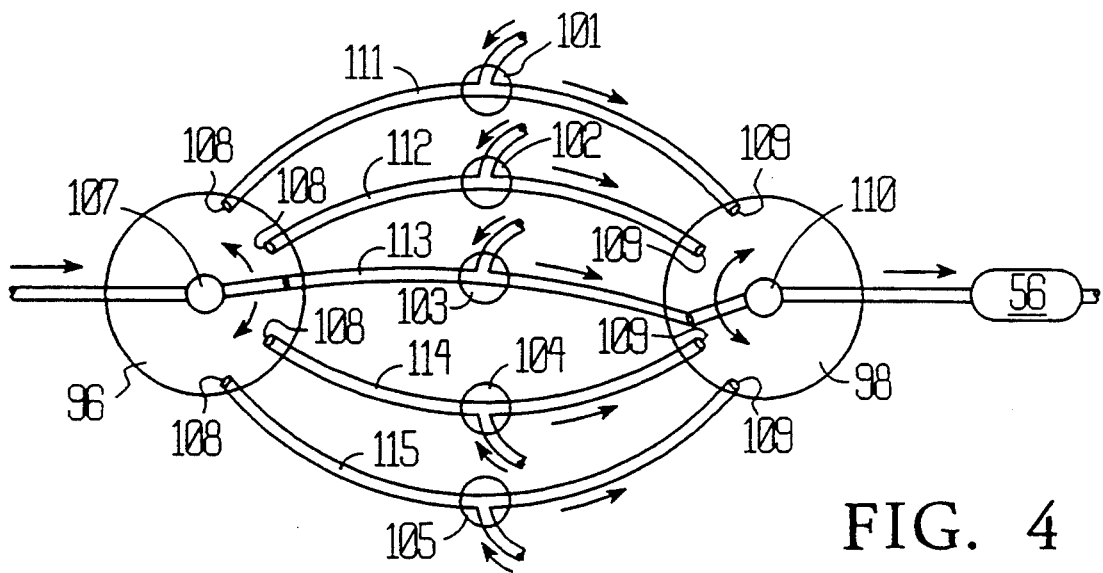
FIG. 4 is a schematic diagram illustrating another embodiment of the present invention in which isolation valves are positioned between two multi-port rotary valve.

Referring to FIG. 4, another embodiment of the present invention is shown which utilizes two rotary valves 96 and 98 and isolation valves 101 to 105 connected therebetween. The rotary valves 96 and 98 in this embodiment can be made simpler than the previous embodiment. The rotary valve 96 has a common inlet 107 and several outlets 108. The flow from the common inlet 107 is selectively directed to the various outlets 108. The rotary valve 98 is arranged in reverse with respect to flow, i.e. there are several inlets 109 and a common outlet 110. Actually, the valves 96 and 98 can be exactly the same but one valve is connected in the flow system in an inverted manner. Isolation valves 101 to 105 are connected intermediate along the fluid branches 111 to 115 between the rotary valves. These isolation valves may be the same as those in the previous embodiment. Reagent reservoirs are connected to the isolation valves in a similar manner as before. The overall function of the configuration shown in FIG. 4 is similar to the function of the rotary valve and isolation valves shown in FIG. 1. By connecting this configuration to the solvent input flow stream (at inlet 58 in FIG. 1) and output flow stream (at outlet 59) to the reaction column 50, reagent delivery can be effected in a similar manner. Both rotary valves 96 and 98 are actuated simultaneously to select a branch for reagent delivery to the reaction chamber 50, as compared to the previous embodiment where a single rotary element is actuated to simultaneously access a pair of ports connected to a branch. FIG. 4 shows the rotary valves selecting branch 113.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific illustrated embodiments, but only by the scope of the appended claims.

I claim:

1. An apparatus for fluid delivery system comprising:
   means for supplying a fluid;
   valve means for selecting flow between common ports, said valve means including a first common port coupled to the supply means, a second common port, a plurality of fluid branches each having two ends in constant flow communication, and means for alternatively selecting fluid flow through a selected fluid branch by connecting flow between the first and second common ports and the two ends of said selected fluid branch, whereby fluid flows through the valve means from the first common port to the second common port through said selected fluid branch; and
   a plurality of isolation valves each coupled along each fluid branch to one of a plurality of different external fluids, each isolation valve operating to control flow of each external fluid into the respective fluid branches, whereby a desired external fluid is delivered through the second common port by connecting the flow between the first and second common ports and the two ends of the fluid branch which is coupled to said desired external fluid by using the valve means and introducing said desired external fluid into said selected fluid branch by controlling the isolation valve coupled to said selected fluid branch.

2. An apparatus for fluid delivery system as in claim 1 wherein the valve means is an integrated rotary valve having means for accessing the two ends of the selected fluid branch simultaneously.

3. An apparatus for fluid delivery system as in claim 1 wherein the valve means comprises first and second valves, the first valve having a common inlet and a plurality of outlets and means for alternatively selecting fluid flow from said common inlet through one of said outlets, the second valve having a plurality of inlets and a common outlet and means for alternatively selecting fluid flow from one of the inlets to the common outlet, whereby each fluid branch is defined between a pair of said plurality of inlets and outlets and the common inlet corresponds to the first common port of the valve means and the common outlet corresponds to the second common port of the valve means, and wherein the isolation valves are each coupled intermediate between a pair of said plurality of inlets and outlets for controlling flow of the external fluid into a selected fluid branch between the first and second valves.

4. An automated chemical reaction processing instrument comprising:
   a main fluid supply;

valve means for selecting flow between common ports, said valve means including a first common port coupled to said main fluid supply, a second common port, a plurality of fluid branches each having two ends in constant flow communication, and means for alternatively selecting fluid flow through a selected fluid branch by connecting flow between the first and second common ports and the two ends of said selected fluid branch, whereby fluid flows through the valve means from the first common port to the second common port through a selected fluid branch;

supply means for supplying different reagents;

a plurality of isolation valves each coupled to the supply means and equidistant between the ends of each fluid branch, each isolation valve operating to control flow of each of said different reagents from the supply means into the respective fluid branches, whereby the different reagents are introduced into the respective fluid branches and delivered through the second common port in sequence by connecting flow between the first and second common ports and the two ends of the fluid branches using said valve means and introducing the reagents into the selected fluid branches by controlling the isolation valves; and means for defining a reaction site coupled to the second common port where the different reagents are delivered in a predetermined sequence for carrying out a desired reaction.

5. An automated instrument as in claim 4 wherein the valve means is an integrated rotary valve having means for accessing the two ends of the selected fluid branch simultaneously.

6. An automated instrument as in claim 4 wherein the valve means comprises first and second valves, the first valve having a common inlet and a plurality of outlets and means for alternatively selecting fluid flow from said common inlet through one of said outlets, the second valve having a plurality of inlets and a common outlet and means for alternatively selecting fluid flow from one of the inlets to the common outlet, whereby each fluid branch is defined between a pair of said plurality of inlets and outlets and the common inlet corresponds to the first common port of the valve means and the common outlet corresponds to the second common port of the valve means, and wherein the isolation valves are each coupled intermediate between a pair of said plurality of inlets and outlets for controlling flow of the external fluid into a selected fluid branch between the first and second valves.

7. An automated instrument as in claim 4 wherein flow distances between the isolation valves and the second common port are substantially the same.

8. An automated instrument as in claim 4 wherein the lengths of the fluid branches are substantially the same.

9. At automated instrument as in claim 4 wherein the reagents are suitable for nucleic acid synthesis.

10. An apparatus for fluid delivery system comprising:

supply means for supplying a first fluid, valve means for selecting flow between common ports, said valve means having an input common port coupled to the supply means, an output common port, and a plurality of branch output ports and a plurality of branch input ports, each said output port being uniquely associated with an input port and in constant flow communication therewith, said valve means including means for selectively connecting said input common port to any one of said branch input ports and said output common port to any one of said branch output ports;

conduit means connecting each of said branch input ports to a respective branch output ports to form a plurality of branches between said input common port and said output common port to allow flow of said first fluid through any one of said branches; and an isolation valve along each of said plurality of branches coupled equidistant between said input ports and output ports, and connected to a respective second fluid, said isolation valve operating to introduce said respective second fluid to the respective branches, whereby any desired one of a plurality of second fluids can be introduced into one of said plurality of fluid branches and delivered through the output common port.

* * * * *